(12) United States Patent
Li et al.

(10) Patent No.: US 7,577,472 B2
(45) Date of Patent: Aug. 18, 2009

(54) MRI METHOD FOR PRODUCING AN INDEX INDICATIVE OF BRAIN DISORDERS

(75) Inventors: Shi-Jiang Li, Brookfield, WI (US); Yin Xu, West Allis, WI (US); Guofan Xu, Wauwatosa, WI (US); Gaohong Wu, New Berlin, WI (US)

(73) Assignee: The MCW Research Foundation Inc., Milwaukee, WI (US)

( * ) Notice: Subject to any disclaimer, the term of this patent is extended or adjusted under 35 U.S.C. 154(b) by 97 days.

(21) Appl. No.: 11/375,347

(22) Filed: Mar. 14, 2006

(65) Prior Publication Data

US 2006/0241382 A1    Oct. 26, 2006

Related U.S. Application Data

(60) Provisional application No. 60/663,091, filed on Mar. 18, 2005.

(51) Int. Cl.
*A61B 5/05* (2006.01)
(52) U.S. Cl. ........................ 600/410; 128/922
(58) Field of Classification Search ............... 600/410, 600/420, 407, 544; 324/309; 128/920
See application file for complete search history.

(56) References Cited

U.S. PATENT DOCUMENTS

| | | | | |
|---|---|---|---|---|
| 5,603,322 | A | * | 2/1997 | Jesmanowicz et al. ...... 600/410 |
| 6,490,472 | B1 | * | 12/2002 | Li et al. ...................... 600/410 |
| 2002/0103428 | A1 | * | 8/2002 | deCharms .................... 600/410 |
| 2002/0103429 | A1 | * | 8/2002 | deCharms .................... 600/410 |
| 2005/0053550 | A1 | * | 3/2005 | Paskavitz et al. ............. 424/9.1 |
| 2005/0197560 | A1 | * | 9/2005 | Rao et al. .................... 600/410 |

OTHER PUBLICATIONS

Neuroradiology, Oct. 2002, vol. 225. No. 1 p. 253-259.*
Francisco Varela, et al; The Brainweb: Phase Synchronization and Large-Scale Integration; Nature Reviews—Neuroscience; vol. 2, Apr. 2001; pp. 229-239.
Gyorgy Buzsaki et al; Neuronal Oscillations In Cortical Networks; Science, vol. 204, No. 5679; pp. 1927-1929; Jun. 25, 2004.
Mark J Lowe et al; Multiple Sclerosis: Low-Frequency Temporal Blood Oxygen Level-Dependent Fluctuations Indicate Reduced Functional Connectivity-Initial Results; Radiology, vol. 224, No. 1; 07-2002; pp. 184-192.
Shi-Jiang Li et al; Alzheimer Disease: Evaluation of A Functional MR Imaging Index As a Marker; Radiology; vol. 225, No. 1; pp. 254-259.
Leaon Glass; Synchronization and Rhythmic Processes in Physiology; Nature, vol. 410, Mar. 8, 2001; pp. 277-284.

(Continued)

*Primary Examiner*—Eric F Winakur
*Assistant Examiner*—Michael T Rozanski
(74) *Attorney, Agent, or Firm*—Quarles & Brady LLP (57) ABSTRACT

Time course MRI data is acquired from the hippocampal region of the brain and processed to produce two indices that are a measure of the functional connectivity between locations therein. The MRI data is acquired while the brain is substantially at rest and the spontaneous low frequency component of the time course data at each location in the hippocampus is extracted and compared in a cross-correlation process. Also acquired is fMRI data which indicates those locations in the brain that should be included in the index calculations.

9 Claims, 8 Drawing Sheets

OTHER PUBLICATIONS

Michael D. Greicius et al; Default-Mode Network Activity Distinguishes Alzheimer's disease from Health Aging: Evidence from Functional MRI ; PNAS; Mar. 30, 2004, vol. 101, No. 13; pp. 4637-4642.

Michael D. Greicius et al; Functional Connectivity in the Resting Brain: A Network Analysis of the Default Mode Hypothesis; PNAS; Jan. 7, 2003, vol. 10, No. 1; pp. 253-258.

Marcus E. Raichle et al; A Default Mode of Brain Function; PNAS; Jan. 16, 2001; vol. 98, No. 2, pp. 676-682.

* cited by examiner

MRI METHOD FOR PRODUCING AN INDEX INDICATIVE OF BRAIN DISORDERS

CROSS-REFERENCE TO RELATED APPLICATIONS

This application claims the benefit of U.S. Provisional patent application Ser. No. 60/663,091 filed on Mar. 18, 2005 and entitled "fMRI-Guided Quantitative Assessment Of The Default Model In the Functional Human Brain".

STATEMENT REGARDING FEDERALLY SPONSORED RESEARCH

This invention was made with government support under Grant No. AG20279 awarded by the National Institute of Health. The United States Government has certain rights in this invention.

BACKGROUND OF THE INVENTION

The field of the invention is the detection of brain disorders using functional magnetic resonance imaging (fMRI) techniques, and particularly the detection of Alzheimer's disease.

Alzheimer's disease is a devastating disease of the brain which results in progressive dementia, physical disability and death over a relatively long period of time. With the aging population in the United States and other countries, the number of Alzheimer's patients is rapidly rising and can accurately be characterized as a silent epidemic. Much research is being conducted to develop drugs that will slow or halt the progression of the disease, and there is hope that a vaccine or inhibitors of secretase may ultimately be developed.

One of the difficulties in managing this disease is the lack of means for its early detection and means for measuring its progression. Such means are needed to identify persons who should receive treatment and to measure the effectiveness of the treatment. An immediate problem is the need for a method which measures the progression of the disease in order to evaluate the effectiveness of the many drugs being developed.

Many techniques have been proposed for detecting and measuring the progress of Alzheimer's disease. These include cognitive tests which attempt to measure brain functions by having the patient perform different tasks. The problem with this approach is that it does not distinguish between dementia caused by Alzheimer's disease and dementia caused by other factors. In addition, the ability to measure the progression of the disease using cognitive tests is very limited.

Neurofibrillary tangles (NFTs) and neuritic plaques (NPs) are the classical neuropathological hallmarks of Alzheimer's disease. Numerous neuropathological studies indicate that the first appearance of NFTs and NPs in the hippocampal region of the brain marks the beginning of the degenerative process. Many studies have been done in which the structure of the brain has been imaged to determine structural changes that are linked to the presence and the progression of Alzheimer's disease. These include: 2-D estimates of size; measures of medial temporal lobe gray matter volume; the qualitative rating of the amount of CSF accumulating in the hippocampal fissures, the size of the suprasellar cistern; and the increased distance between the right and left uncus. None have been particularly successful, and in fact, it has been found that profound structural changes can occur in the brain of some individuals with no cognitive impairment or other symptoms of the disease being evident.

It has been suggested that with progression of Alzheimer's disease, the increased presence of NFTs and NPs in the hippocampus disrupt the perforant pathway and affect functional connectivity. A number of methods have been proposed to assess the functional connectivity in the hippocampal region. The concept of functional connectivity is widely applied to electroencephalogram (EEG) coherence, where it is a measure of the synchronization between two signals across distinct regions of the human brain and is interpreted as an expression of their functional interaction. In positron emission tomography studies, functional connectivity is defined as a spatiotemporal correlation between spatially distinct regions of cerebral cortex. Positron emission tomography (PET) and single photon emission computed tomography (SPECT) can be used to monitor regional cerebral glucose metabolism (rCMRglc) and regional cerebral blood flow (rCBF). It has been found that significant hypoperfusion and hypometablism occur in the region of temporal and parietal association cortices in probable Alzheimer's patients. Many studies have demonstrated the correlation between regional localized hypoperfusion and hypometablism with cognitive deficits seen on behavioral testing. Despite frequent reports of abnormal function in Alzheimer's patients observed by PET and SPECT, however, the clinical utility of these methods is still controversial.

Functional magnetic resonance imaging (fMRI) technology provides a new approach to study neuronal activity. Conventional fMRI detects changes in cerebral blood volume, flow, and oxygenation that locally occur in association with increased neuronal activity induced by functional paradigms. As described in U.S. Pat. No. 5,603,322, an MRI system is used to acquire signals from the brain over a period of time. As the brain performs a task, these signals are modulated synchronously with task performance to reveal which regions of the brain are involved in performing the task. Much research has been done to find tasks which can be performed by patients, and which reveal in an fMRI image acquired at the same time, regions in the brain that function differently when Alzheimer's disease is present.

In U.S. Pat. No. 6,490,472 an fMRI method is described for producing an indication of the presence and the progress of a brain disorder by measuring the functional connectivity at different locations while the brain is substantially at rest. An index called the "COSLOF" index is calculated from the time course fMRI data acquired from a selected region of the brain and a strong correlation was found between this index and the presence of Alzheimer's disease.

The COSLOF index method has two limitations. First, it is very difficult to accurately identify the voxels in the brain that should be included in the calculation of the index. And second, the SNR of the acquired BOLD signal is very low and this impairs the accurate calculation of the COSLOF index. As a result, the COSLOF index is useful in identifying patients with Alzheimer's disease, but it is not sensitive enough to identify patients with mild cognitive impairment ("MCI") who will eventually evidence Alzheimer's disease. The identification of MCI patients is very important, since it is these patients who should receive treatment before Alzheimer's disease more significantly impairs the brain.

SUMMARY OF THE INVENTION

The present invention is a method and system for producing an indication of the presence and the progress of a brain disease or disorder by measuring the functional connectivity at different locations therein. More specifically, the present invention is an improvement in prior methods which enables a more precise identification of the locations in the brain that should be included in the measurement, and an improvement in the measurement itself.

One aspect of the invention is the more precise identification of locations, or voxels, in the brain that should be included in the connectivity measurement. This is achieved by acquiring functional MRI data from the brain which indicates those locations that may be impaired by the disease being investigated. In the case of MCI and Alzheimer's disease, for example, memory tasks are employed in a prescribed alternating pattern to stimulate a BOLD response in and around the hippocampal region of the brain. Voxels which exhibit the prescribed BOLD stimulation pattern in fMRI images are identified for inclusion in the connectivity index calculation. This voxel selection process eliminates from the calculation many voxels which are irrelevant and it enables the region of the brain to be expanded beyond the physical boundary of a particular structure such as the hippocampus without diluting the sensitivity of the connectivity index.

The invention enables a connectivity index to be calculated in regions of the brain between anatomically identifiable regions of the brain. For example, it has been discovered that Alzheimer's disease significantly impacts regions around the hippocampus which cannot be precisely identified in an MRI anatomical image. The inclusion of these surrounding regions enhances the sensitivity of the connectivity index measurement to this disease and the present invention excludes from the computation many included voxels that are not relevant to the computation.

Another aspect of the present invention is an improved method for calculating the connectivity index. Low frequency component voxel vectors are produced from time course MRI data acquired from the subject's brain. These low frequency component voxel vectors are limited to time course signals in a narrow frequency range (e.g., 0.015 to 0.1 Hz). It has been discovered that even with this limited pass band significant noise is included in the low frequency component voxel vectors. An improved connectivity index called the "Phase Delay Index" or "PDI" has been derived which suppresses much of this noise and increases the SNR of the connectivity index measurement. This index measures connectivity between regions of the brain when the brain is at rest or when it is performing cognitive tasks.

GENERAL DESCRIPTION OF THE INVENTION

In U.S. Pat. No. 6,490,472 a method is described for producing an index which is a measure of the functional connectivity between locations in the hippocampal region of the brain. Referred to in the art as the "COSLOF" index, the value of this connectivity index has been found to correlate with the presence of Alzheimer's disease. The COSLOF index, ("CI"), was calculated from a matrix of pair-wise cross-correlation coefficients of all of the voxels from a region of interest (ROI), $$CI = \frac{2}{K(K-1)} \sum_{i,j=1, i>j}^{K} cc_{ij} \qquad (1)$$

where K was the number of the selected voxels. The cross-correlation coefficient $cc_{ij}$ was calculated between measured voxel time courses of $s_i(t)$ from the $i^{th}$ voxel and of $s_j(t)$ from the $j^{th}$ voxel (i, j=1, 2, . . . K, i≠j) as follows:

$$cc_{ij} = \frac{E(s_i(t) \cdot s_j(t))}{\sqrt{\text{Var}(s_i(t)) \cdot \text{Var}(s_j(t))}}. \qquad (2)$$

Here the mean values of $s_i(t)$ and $s_j(t)$ are set to zero, and E( ) and Var( ) are the mean value and the variance of the voxel time course, respectively. To determine which of the three factors (difference in the fluctuation intensity, difference in frequency components and difference in phase delay among the voxel time courses) would be the main mechanism to significantly affect $cc_{ij}$ and the COSLOF index, the following theoretical analyses is presented.

First, consider how the magnitude of the time course vectors, or spontaneous low frequency components ("SLF") thereof affect the COSLOF indices. The SLF has characteristics of a BOLD-like signal mixed in with physiological noise. If SLF is defined as the signal, then the signal and noise model in a voxel time course can be expressed as:

$$s_M = s_L + n_0 \qquad (3)$$

where $s_M$ is the total measured signal and noise after a Hamming filter with a pass band of 0.015~0.1 Hz, $s_L$ represents the SLF signal with a standard variation of $\sigma_L$, and $n_0$ represents the thermal noise with a standard variation of $\sigma_0$. The $S_m$ two components can be taken as mutually independent. Incorporating Eq. (3) into Eq. (2), a new expression of $cc_i$ is obtained:

$$cc_{ij} = \frac{E(s_{Li}(t) \cdot s_{Lj}(t))}{\sqrt{(\sigma_{Li}^2 + \sigma_0^2)(\sigma_{Lj}^2 + \sigma_0^2)}}. \qquad (4)$$

The noise factor $\sigma_0$ will thus affect the calculation of the cross-correlation coefficient. According to Eq. (4), a higher signal-to-noise ratio (SNR), (η) may lead to higher values of cross-correlation coefficients, and also higher COSLOF indices. To obtain a cross-correlation coefficient without this noise factor (or without the impact of SNR), $ncc_{ij}$, the calculated $cc_{ij}$ in Eq. (4) was normalized with a factor expressed in Eq. (5) below.

$$ncc_{ij} = \frac{E(s_{Li}(t) \cdot s_{Lj}(t))}{\sigma_{Li} \cdot \sigma_{Lj}} = cc_{ij} \cdot \frac{\sqrt{(\eta_i^2+1)(\eta_j^2+1)}}{\eta_i \cdot \eta_j} \quad (5)$$

where SNR is defined as $\eta = \sigma_L/\sigma_0$. Thus, this normalization depresses the impact of different SNR from subjects. The noise $\sigma_0$ can be estimated from filtered voxel time courses outside the brain region where there are no imaging ghosts. Since the measured noise $\sigma_M$ in the masked region (outside brain region) is Rayleigh distributed, the $\sigma_0$ is estimated based on Eq. (6):

$$\sigma_0 = \sigma_M/\sqrt{2-\pi/2} \quad (6)$$

where $\sigma_M^2$ is the measured variance of the voxel time courses in the masked noise region and the noise $\sigma_0$ inside the brain regions with high SNR is normally distributed.

Another factor, that can affect the cross-correlation coefficient of SLF components in the voxel time courses, is the distribution of the power spectrum in the frequency domain. Assuming two noise-free signal time courses have one matching frequency component $f_0$ (with standard deviation $d_1$), and each, respectively, has a different frequency component $f_1$ and $f_2$ with the same standard deviation $d_2$, denoted as:

$$s_i(t) = \sqrt{2}d_1 \cos(2\pi f_0 t) + \sqrt{2}d_2 \cos(2\pi f_1 t)$$
$$s_j(t) = \sqrt{2}d_1 \cos(2\pi f_0 t) + \sqrt{2}d_2 \cos(2\pi f_2 t), \quad (7)$$

then the cross-correlation is:

$$cc_{ij} = \frac{E(s_i(t) \cdot s_j(t))}{\sqrt{\text{Var}(s_i(t)) \cdot \text{Var}(s_j(t))}} = \frac{d_1^2}{d_1^2 + d_2^2}. \quad (8)$$

Equation (8) shows that different frequency distributions may lead to different cross-correlation coefficients and COSLOF index.

Besides the two possible factors described above, the cross-correlation coefficient can be taken as a measurement of synchrony between two voxel time courses. For simplicity, assume the detected voxel-wise signal $s_L$ is from an original signal $s_o$, which is stationary, and identical for each voxel. The signal $s_L$ is a result of convolution of $s_o$ with a response function, $H_i(f)$, which represents the linear time-invariant system with respective linear phase shift for each voxel. The frequency domain form of the response function of $i^{th}$ voxel is denoted as:

$$H_i(f) = P(f)\exp(-j2\pi t_i f) \quad (9)$$

where $P(f)$ is the kernel function of the response function and is assumed to be the same for all voxels, while $t_i$ is the time-delay parameter.

In the frequency domain, the cross-correlation of the two voxel time courses can be expressed as follows:

$$E(s_{Li}(t) \cdot s_{Lj}(t)) = R_{ij}(0) = \int_{-\infty}^{\infty} S_{ij}(f) df \quad (10)$$

where $R_{ij}(0)$ is a correlation function without time shift, and $S_{ij}(f)$ is the cross-spectral density which can be calculated as:

$$S_{ij}(f) = H_i(f)\overline{H_j(f)}S_{OO}(f) \quad (11)$$

where $S_{OO}(f)$ is the power spectral density of the SLF. $P(f)$ and $S_{OO}(f)$ have the following properties:

$$P(f) = P(-f)$$
$$S_{OO}(f) = S_{OO}(-f) \quad (12)$$

Combining Eqs. (9-12), we have:

$$R_{ij}(0) = \int_{-\infty}^{\infty} |P(f)|^2 S_{oo}(f)\exp(-j2\pi\Delta t_{ij}f) df \quad (13)$$
$$= \int_{-\infty}^{\infty} |P(f)|^2 S_{oo}(f)(\cos(2\pi\Delta t_{ij}f) - j\sin(2\pi\Delta t_{ij}f)) df$$
$$= \int_{-\infty}^{\infty} |P(f)|^2 S_{oo}(f)\cos(2\pi\Delta t_{ij}f) df$$

where $\Delta t_{ij} = t_i - t_j$, which is the time delay between the time courses i and j. To reach a maximum cross-correlation coefficient, we can shift a voxel time course by $\tau^m$ and make $\Delta t_{ij}$ = zero. Here $\tau^m$ is generally recorded as the shifted time points required to obtain a maximum cross-correlation between voxel time courses i and j. A correlation function with time shift of $\tau^m$ is generated as shown below:

$$R_{ij}(\tau^m) \geq R_{ij}(\tau) = E(s_{Li}(t) \cdot s_{Lj}(t+\tau)), 0 < \tau < \frac{1}{f_L} \quad (14)$$
$$= \tau^m = \arg\left(\max_{0<\tau<T} E(s_{Li}(t) \cdot s_{Lj}(t+\tau))\right)$$

where $f_L = 0.015$ Hz, which is the lower limit of the pass band of the filter. When $\Delta t_{ij}$ is set to zero, the maximum-shifted cross-correlation is:

$$cc_{ij}^m \propto \max_{0<\tau<T} E(s_{Li}(t) \cdot s_{Lj}(t+\tau)) = \int_{-\infty}^{\infty} |P(f)|^2 S_{LL}(f) df \quad (15)$$

Similar to Eq. (1), the COSLOF index under the maximum-shifted condition can be defined as:

$$CI^m = \frac{2}{K(K-1)} \sum_{i,j=1,i>j}^{K} cc_{ij}^m. \quad (16)$$

The ratio of $cc_{ij}$ to $cc^m_{ij}$ is as follows:

$$r_{ij} = \frac{cc_{ij}}{cc_{ij}^m} = \frac{\int_{-\infty}^{\infty} |P(f)|^2 S_{oo}(f)\cos(2\pi\Delta t_{ij}f) df}{\int_{-\infty}^{\infty} |P(f)|^2 S_{oo}(f) df} \quad (17)$$
$$= \frac{\int_{f_L}^{f_H} |P(f)|^2 S_{oo}(f)\cos(2\pi\Delta t_{ij}f) df}{\int_{f_L}^{f_H} |P(f)|^2 S_{oo}(f) df}$$

This ratio becomes a mono-variable function of $\Delta t_{ij}$. If the time course voxel vector is simply a sine or cosine wave, $r_{ij}$ in Eq. (17) is a cosine function of the phase delay of the two time courses. We define $\theta_{ij}$ as the phase delay (PD) between two time courses and calculate as follows:

$$\cos\theta_{ij} = r_{ij} = \frac{cc_{ij}}{cc_{ij}^m} \Rightarrow \theta_{ij} = \cos^{-1}\left(\frac{cc_{ij}}{cc_{ij}^m}\right) \qquad (18)$$

For all voxel time courses in the selected region, the averaged PD is defined as the phase delay index (PDI) in order to measure the extent of functional synchrony in the selected region. The PDI, $\theta_G$ is calculated as follows:

$$\theta_G = \overline{\theta_{ij}} = \frac{2}{K(K-1)} \sum_{i,j=1,i>j}^{K} \cos^{-1}\left(\frac{cc_{ij}}{cc_{ij}^m}\right) \approx \cos^{-1}\left(\frac{CI}{CI^m}\right) \qquad (19)$$

By considering the noise effect on $cc^m{}_{ij}$ and applying Eq. (5), the normalized maximum noise-free cross-correlation $ncc_{ij}{}^m (= cc_{ij}{}^m(\infty))$ is:

$$ncc_{ij}^m = cc_{ij}^m(\infty) = cc_{ij}^m(\eta = \infty) = cc_{ij}^m(\eta_i,\eta_j) \cdot \frac{\sqrt{(\eta_i^2+1)\cdot(\eta_j^2+1)}}{\eta_i\eta_j} \qquad (20)$$

where $cc_{ij}{}^m(\infty)$ is denoted as noise-free cross-correlation, while $cc_{ij}{}^m(0)$ is for pure noise. By applying Eq. (20) to Eqs. (18) and (19), the PDI can be rewritten as:

$$\theta_G = \frac{2}{K(K-1)} \sum_{i,j=1,i>j}^{K} \cos^{-1}\left(\frac{ncc_{ij}}{cc_{ij}^m(\infty)}\right) \qquad (21)$$

$$= \frac{2}{K(K-1)} \sum_{i,j=1,i>j}^{K} \cos^{-1}\left(\frac{cc_{ij}}{cc_{ij}^m}\right) \approx \cos^{-1}\left(\frac{CI}{CI^m}\right)$$

where K is the total number of selected voxels.

Comparing Eq. (19) and Eq. (21), the PDI is a normalized index, and not sensitive to noise factors. It provides a better connectivity index to directly quantify the synchrony between voxel time courses.

DETAILED DESCRIPTION OF THE PREFERRED EMBODIMENT

Figure 1:
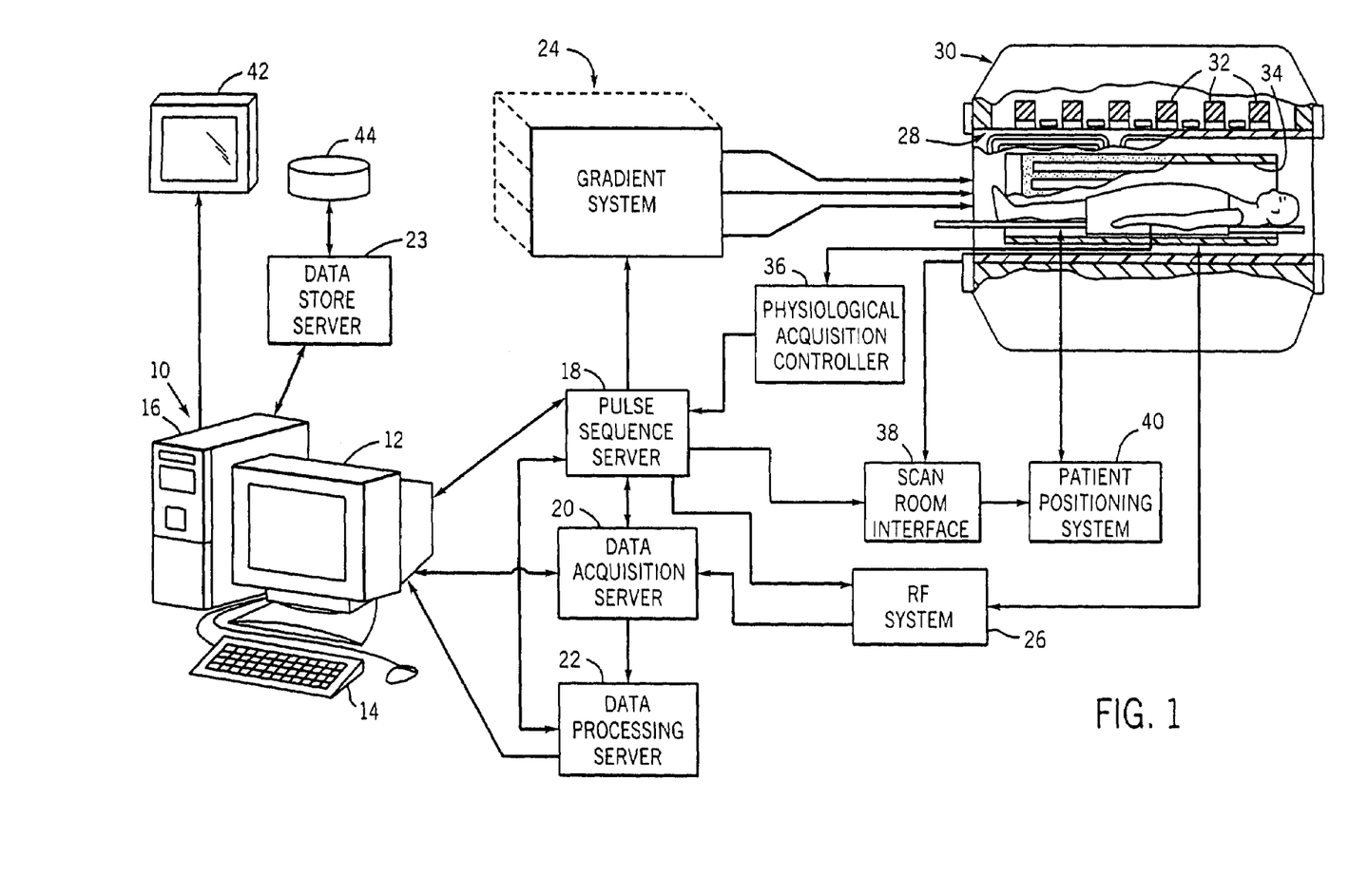
FIG. 1 is a block diagram of a preferred MRI system used to practice the present invention.

Referring particularly to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

To practice the present invention a local head coil is used in place of the whole body rf to receive the NMR signals produced in the brain. In the preferred embodiment a local gradient coil and end-capped birdcage RF coil such as that disclosed in U.S. Pat. No. 5,372,137 is employed and is incorporated herein by reference.

Figure 2:
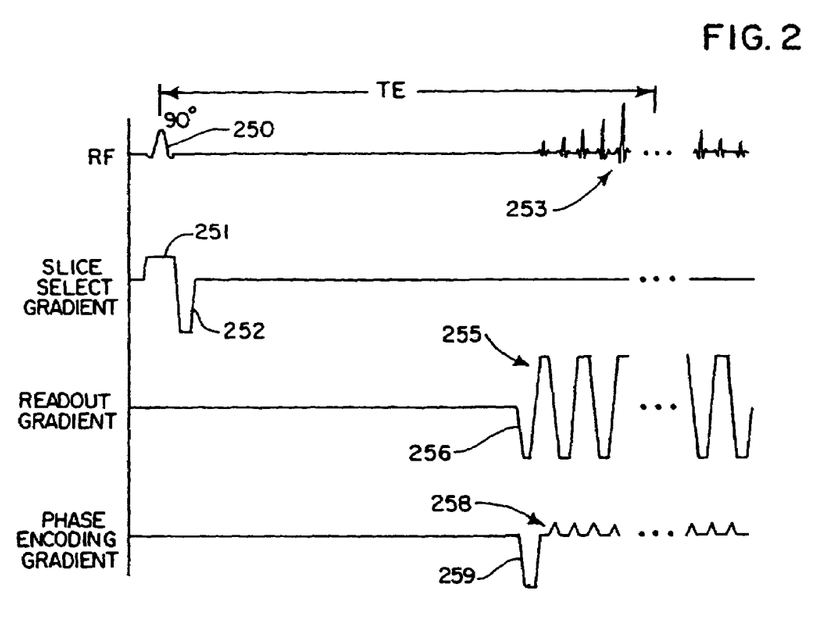
FIG. 2 is a graphic representation of a pulse sequence performed by the MRI system of FIG. 1 to practice the present invention.

The EPI pulse sequence employed in the preferred embodiment of the invention is illustrated in FIG. 2. A 90° RF excitation pulse 250 is applied in the presence of a Gz slice select gradient pulse 251 to produce transverse magnetization in a slice through the brain ranging from 4 to 25 mm thick. The excited spins are rephased by a negative lobe 252 on the slice select gradient Gz and then a time interval elapses before the readout sequence begins. A total of 64 separate NMR echo signals, indicated generally at 253, are acquired during the EPI pulse sequence. Each NMR echo signal 253 is a different view which is separately phase encoded to scan ky-space from ky=−32 to ky=+31 in monotonic order. The readout sequence is positioned such that the view acquired at ky=0 occurs at the desired echo time (TE). In the preferred embodiment an EPI pulse sequence with TE=40 ms and TR=2 sec. is used. An in-plane resolution of 3.75 mm, a field of view of 24 cm and a slice thickness of 6 mm are used.

The NMR echo signals 253 are gradient recalled echo's produced by the application of an oscillating Gx readout gradient field 255. The readout sequence is started with a negative readout gradient lobe 256 and the echo signals 253 are produced as the readout gradient oscillates between positive and negative values. A total of 64 samples are taken of each NMR echo signal 253 during each 512 microsecond readout gradient pulse 255. The successive 64 NMR echo signals 253 are separately phase encoded by a series of Gy phase encoding gradient pulses 258. The first pulse is a negative lobe 259 that occurs before the echo signals are acquired to encode the first view at ky=−32. Subsequent phase encoding pulses 258 occur as the readout gradient pulses 255 switch polarity, and they step the phase encoding monotonically upward through ky space.

At the completion of the EPI pulse sequence, therefore, 64 separate frequency encoded samples of 64 separately phase encoded NMR echo signals 253 have been acquired. This 64×64 element array of complex numbers is Fourier transformed along both of its dimensions (ky and kx) to produce a 64×64 element array of image data that indicates the NMR signal magnitude along each of its two dimensions (y and x).

In order to suppress the signal from cerebral spinal fluid, the EPI pulse sequence may be preceded by an inversion recovery preparation pulse sequence. As is well known in the art, inversion recovery pulse sequences include a 180° rf excitation pulse that inverts the longitudinal spin magnetization, followed by a recovery period TI in which the longitudinal magnetization of the desired spin species recovers, but that of undesired spin species does not. In the preferred embodiment TI is set to 750 milliseconds to suppress the longitudinal magnetization of cerebral spinal fluid spins prior to performing each EPI pulse sequence.

In the preferred embodiment of the invention the EPI pulse sequence is repeated over a 10.5 minute time period to acquire time course NMR data. During a first period of 6 minutes the pulse sequence is repeated 180 times to acquire 180 sagittal slice images which are used to calculate the connectivity index as described below. During a second 4.5 minute period an additional 135 sagittal slice images are acquired while the patient performs tasks or is stimulated in a prescribed pattern. These 135 images are used to produce fMRI images that are used to identify voxel locations in the brain that should be included in the connectivity index calculation.

In the preferred embodiment two tasks are alternately performed for 30 seconds each during the second 4.5 minute period to test the memory "circuitry" around the hippocampus and the medial temporal lobe. Two memory tasks are used in which Task A involves episodic memory formation that modulates neural activity in the target region above the resting state and Task B involves perceptual discrimination which modulates neural activity in the target region to a much lower state.

Specifically, in Task A, the subject is shown a series of novel color pictures of easily recognizable indoor and outdoor scenes. The stimuli are salient, recognizable and meaningful to the viewer, thereby increasing neural activity in episodic memory structures. Each picture is presented for three seconds. The subject is asked to recognize whether the pictures depict an indoor or outdoor scene by pressing predefined buttons on a response box.

Task B serves as the contrast task for Task A. The stimuli in Task B are relatively devoid of recognizability and meaning. In Task B, subjects are shown the same series of pictures in Task A after the images have been scrambled into small tiles so that the pictures are no longer recognizable. This is done to control overall luminescence and color saturation between the two tasks. The scrambled color images are configured in a square and a vertical red line is then placed near the middle of the square picture, either to the left or right of center. An 8% difference between the areas of the left and right sides results. Each image is presented for three seconds and the subject is asked to indicate which side of the square appeared larger (a perceptual discrimination) by pressing one of two predefined buttons on the response box.

Each task was compiled on a laptop computer using E-Prime software (Psychology Software Tools, Inc., Pittsburg, Pa.) and the pictures are projected onto a screen at the end of the imaging table with a computer-controlled projector (Epson ELP 5000) in the scanner room. The subject views these images during the scan using a scope such as that described in U.S. Pat. No. 5,339,813.

The acquired NMR data is processed in the conventional manner to produce an NMR image data set for 315 images. As explained above, a two dimensional Fourier transformation is performed by the data processing server 22 (FIG. 1) and the resulting NMR image data set is stored for further processing by the data store server 23 according to the present invention.

Figure 3:
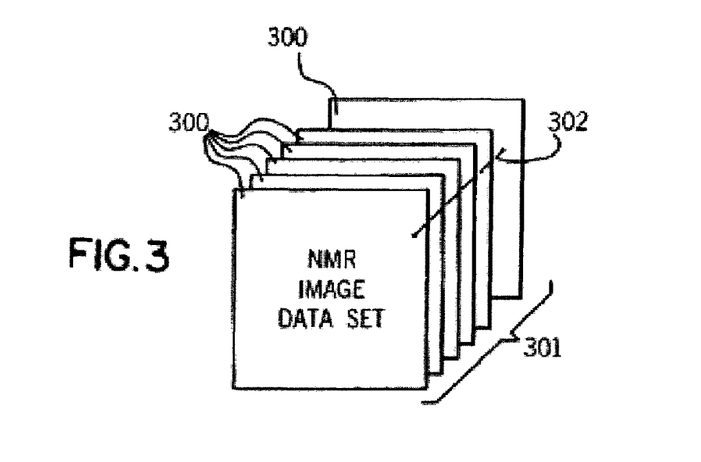
FIG. 3 is a pictorial representation of data acquired by the MRI system of FIG. 1.

Referring to FIG. 3, this NMR image data set is organized as a set of 64×64 element 2D arrays 300 in which each element stores the magnitude of the NMR signal from one voxel in the scanned slice. Each array 300 can be used to directly produce a 256×256 pixel anatomical image of the brain slice for output to the video display 12. While each array 300 is a "snap shot" of the brain slice at a particular time during the time course study, the NMR image data set may also be viewed as a single 64×64×315 3D array 301 in which the third dimension is time.

The time course NMR data for one voxel in the array 301 is referred to herein as a time course voxel vector. One such 315 element vector is illustrated in FIG. 3 by the dashed line 302. Each time course voxel vector 302 indicates the magnitude of the NMR signal at a voxel in the image slice over the time course study. One such time course voxel vector is shown graphically in FIG. 4, where the NMR signal magnitude indicates neuronal activity in one brain voxel during the 6 minute period 1 of the scan, and it indicates substantial variation in neuronal activity during the 4.5 minute period 2 of the scan.

Figure 5:
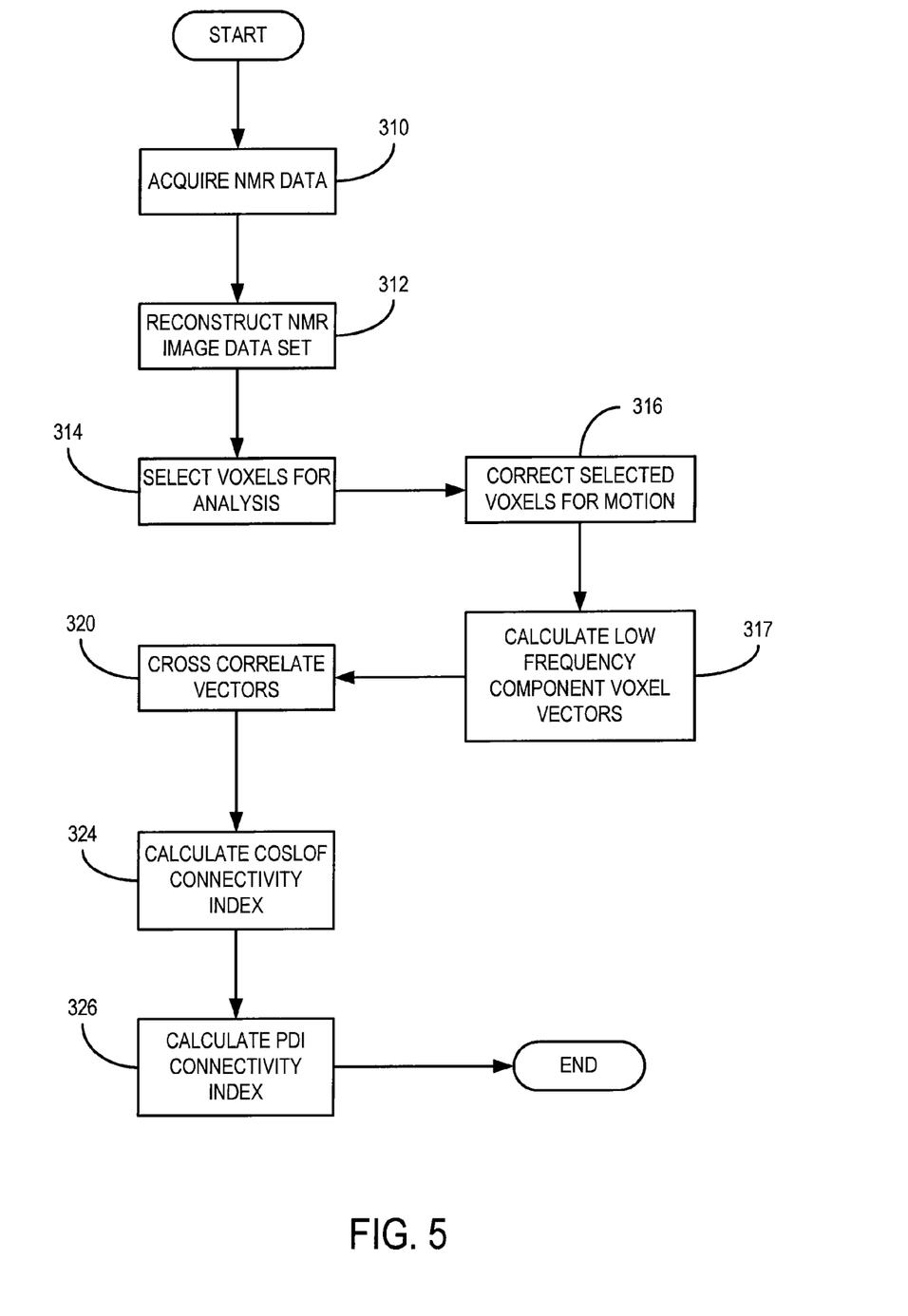
FIG. 5 is a flow chart which illustrates the steps performed when practicing a preferred embodiment of the invention.

The acquisition of the array of time course data 301 and the processing of that data to produce a connectivity index that is indicative of a brain disorder or disease is performed under the direction of programs executed by the MRI system. The steps performed while practicing a preferred embodiment of the invention are set forth in FIG. 5. Referring particularly to FIG. 5, the first step in producing a connectivity index is to acquire time course image data from the patient's brain as indicated at process block 310. Foam padding is employed to limit head motion within the local head coil and then localized T1-weighted axial and sagittal plane slices are acquired to provide anatomic images which help define the number of slices and their location for the time course NMR image data acquisition. The above-described EPI pulse sequence is then used as described above. Each session requires about 10.5 minutes to acquire 15 sagittal slices, with 315 images for each slice. Each of the 15 slices are acquired in an interleaved manner such that the resulting NMR data for each slice is acquired over substantially the same time period. The acquired images are reconstructed as indicated at process block 312 and described above to form the time course NMR image data set 301. In addition, $B_0$ field correction is made by using variable TE at the end of the acquisition series and its phase maps.

Figure 6:
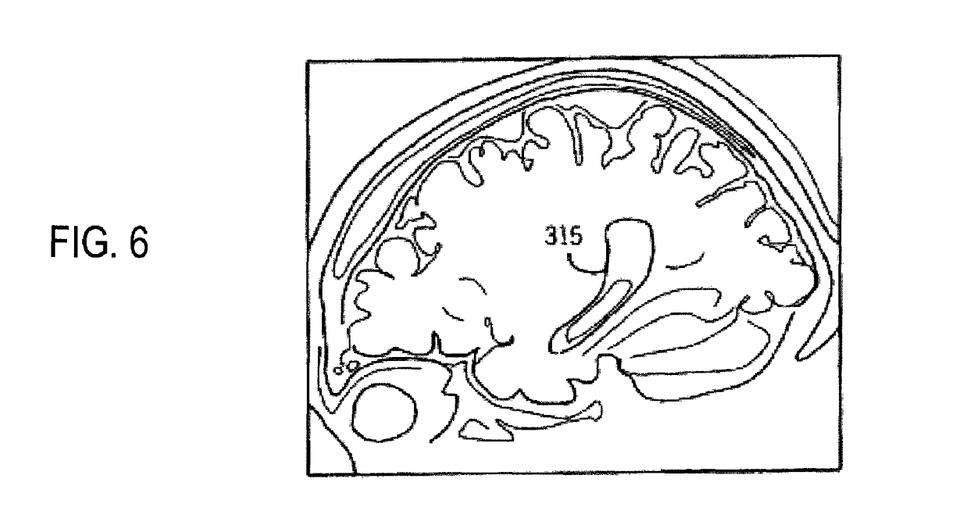
FIG. 6 is a pictorial representation of an anatomical image used to carry out a step in the procedure of FIG. 5.
Figure 8:
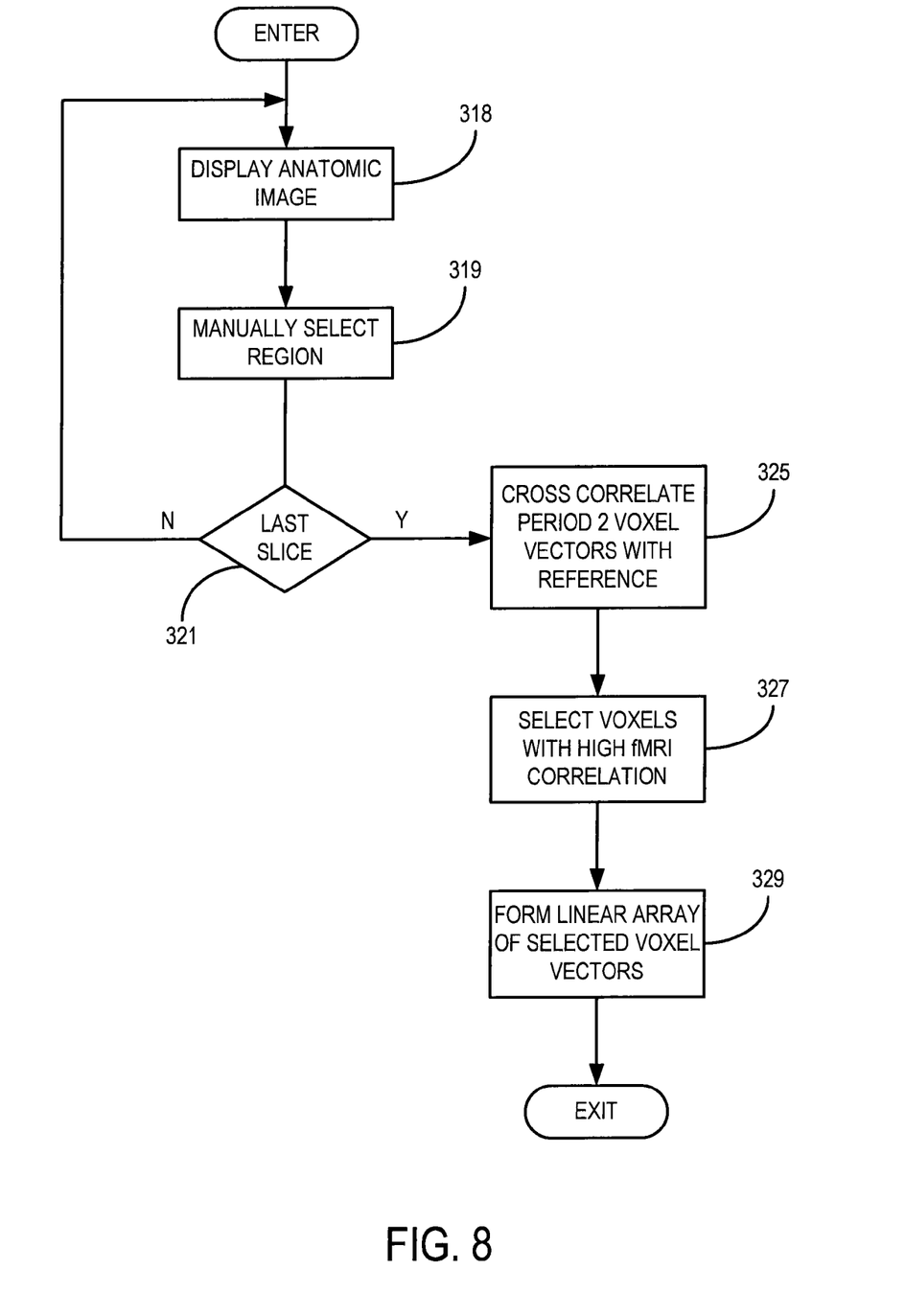
FIG. 8 is a flow chart of steps performed in one of the steps indicated in FIG. 5.

Using the acquired anatomic images and the data acquired in period 2, the voxels to be included in the connectivity index measurement are selected next as indicated at process block 314. As indicated in FIG. 8 at process block 318 an anatomic image for each acquired slice is displayed and the voxels contained in the hippocampal region are selected by the operator at process block 319. A track ball is used to move a cursor over each selected voxel in the anatomical image to identify a region 315 as shown in Fig 6. This region, 315, may not only include the hippocampus but also surrounding structures that are deemed relevant to the connectivity measurement being made. This selection process is repeated for each of the 15 sagittal slices as indicated at decision block 321 such that all the voxels contained in the hippocampus plus voxels in the surrounding regions are selected. It has been discovered that in addition to the connectivity between voxels within the hippocampus, the connectivity between voxels in the hippocampus and structures in the surrounding regions are important indicators of Alzheimer's disease and MCI. Such structures include parahippocampus, entorhinal cortex, poterio cingulate, and precuneus, and since these are difficult to identify and segment, it is contemplated that the selected region 315 will be larger than needed and will include voxels that are not involved in the neuronal activity being tested.

Figure 4:
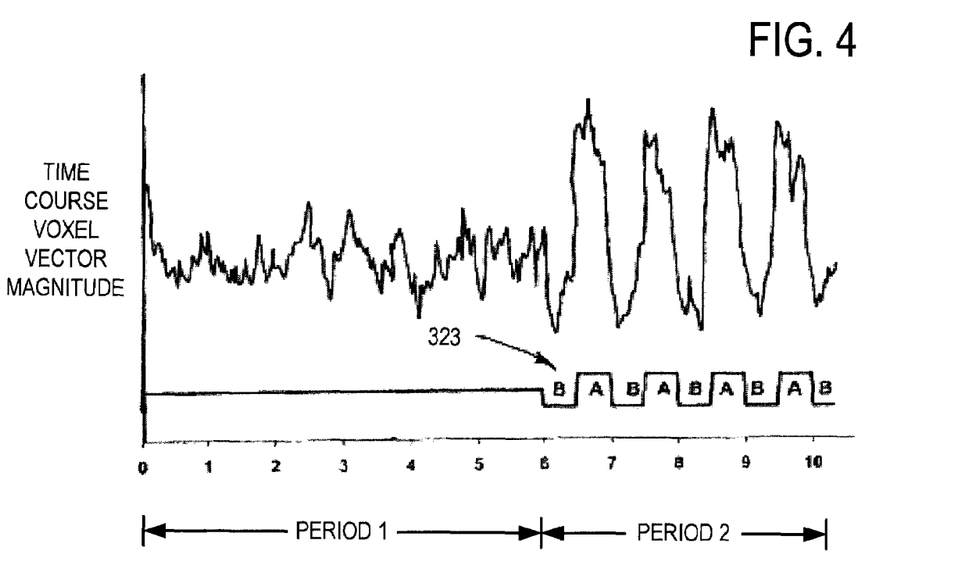
FIG. 4 is a graphic representation of the signal formed by one voxel vector in the data of FIG. 3.

To further limit the selection of voxel vectors to be included in the connectivity calculations the fMRI data acquired during period 2 is used to identify involved voxels. As shown in FIG. 4, voxels which are involved with the neuronal activity produced by Tasks A and B will reveal fluctuations in the NMR signal magnitude during period 2 that correlate with a reference voxel vector indicated at 323. The reference voxel vector 323 is an oscillating waveform that corresponds in frequency with the alternating 30 second applications of Tasks A and B. As shown in FIG. 8, the cross-correlation of each voxel vector (period 2 data only) in the selected region 315 (FIG. 6) with this reference voxel vector 323 is calculated as indicated at process block 325. As described in U.S. Pat. No. 5,603,322 entitled "Time Course MRI Imaging Of Brain Functions", which is incorporated herein by reference, this is a calculation which indicates the degree of waveform shape similarly between the two vectors. Those voxel vectors which show a high correlation with the reference vector 323 are active in the neuronal activity produced by Tasks A and B. As indicated at process block 327, those voxel vectors inside the selected region 315 with a correlation over 0.23 ($P<0.01$) are selected for inclusion in the connectivity index calculations. The period 1 data in these "N" selected voxel vectors 302 are then arranged in a linear array 335 illustrated in FIG. 7 as indicated at process block 329.

As indicated at process block 316 in FIG. 5, the voxel vectors 302 for the selected pixels are corrected for possible patient motion during the scan. This procedure is performed on the period 1 data in the voxel vectors 302. In the preferred embodiment this is accomplished using orthognization and the method disclosed by R. W. Cox in *Comput. Biomed. Respectively.* 1996; 39:162-73 entitled "*AFNI: Software for Analysis and Visualization of Functional Magnetic Reso-*

*nance Neuroimages*", although other motion correction methods known in the art may also be employed. Within each period 1 of time course voxel vector 302 there are also temporal components that correspond to the cardiac and respiratory frequencies, CSF pulsatile motion, and other physiological noise and these are also removed to the extend possible.

As indicated at process block 317, the next step in the process is to produce a set of spontaneous low frequency component voxel vectors from the period 1 data in linear array 335. Once the voxel locations are selected, the initial 6-minute voxel time courses in each scan are filtered with a 9-point Hamming bandpass filter with a pass-band of 0.015 to 0.1 Hz. The filtered voxel time courses are referred to herein as spontaneous low frequency component voxel vectors, or "SLOs". We hypothesize that this component arises from fluctuations in capillary blood flow and oxygenation, which are secondary to neuronal activity.

Figure 7:
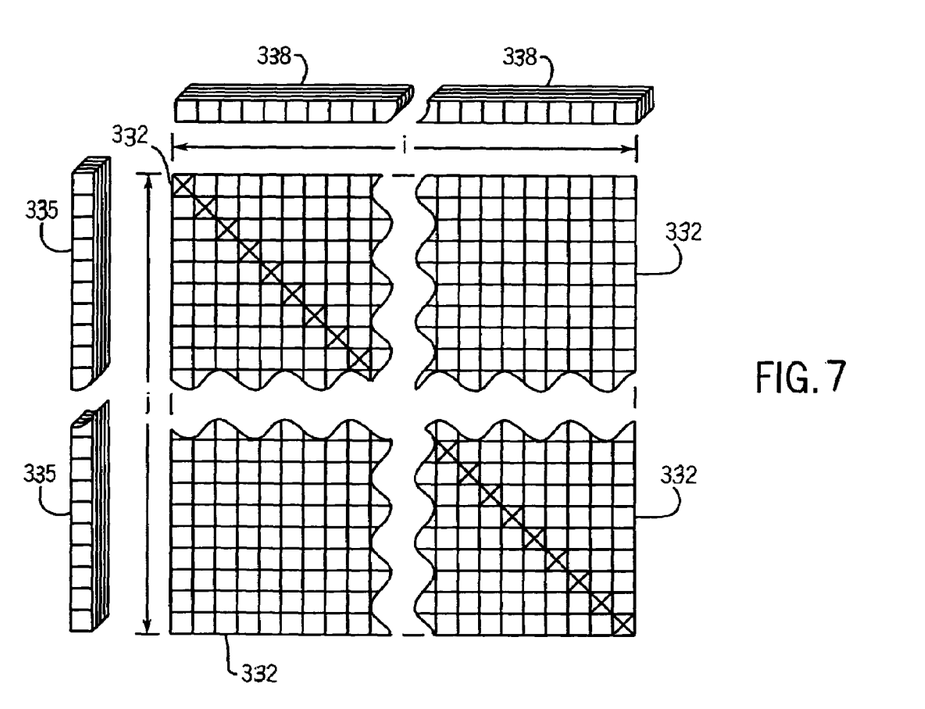
FIG. 7 is a pictorial representation of data structures produced when performing the procedure of FIG. 5.

As shown in FIG. 7, the resulting N spontaneous low frequency component voxel vectors are organized in a linear array 338 which corresponds to the linear array 335 of selected voxel vectors from which they are produced. As indicated in FIG. 4 at process block 320, the next step is to calculate the cross-correlation coefficient between each of the N vectors in the array 338 with each of the N vectors in the array 335. In other words, calculate the cross-correlation of the spontaneous low frequency component in each selected voxel with the period 1 time course voxel vector of every selected voxel. In the preferred embodiment the cross-correlation is performed as described in U.S. Pat. No. 5,603,322. With this method the correlation is measured by calculating the dot product of the two vectors. It can be appreciated by those skilled in the art that any method which compares a time course voxel vector with a spontaneous low frequency component voxel vector and produces an indication of the degree of similarity in the two vectors will provide the desired connectivity indication.

A correlation coefficient matrix 332 is produced in which each ij element therein is a result of the cross-correlation of the $i^{th}$ spontaneous low frequency component voxel vector and the $j^{th}$ time course voxel vector. Note that the diagonal values in this matrix are cross-correlating the same voxels, and for this reason these values are eliminated from the following calculations. The matrix 332 corresponds to $CC_{ij}$ in the above equations.

As indicated at process block 324, the next step is to calculate the COSLOF connectivity INDEX. This is done using the data CCij in the matrix 332 as described in U.S. Pat. No. 6,490,472 entitled "MRI System And Method For Producing An Index Indicative Of Alzheimer's Disease," which is incorporated herein by reference. Then, as indicated at process block 326 and described in more detail below, the PDI connectivity index is calculated using the same data CCij in matrix 332. The calculated connectivity indices are displayed and printed in a report, and together, they provide information which aids in the diagnosis of Alzheimer's disease and MCI.

Figure 9:
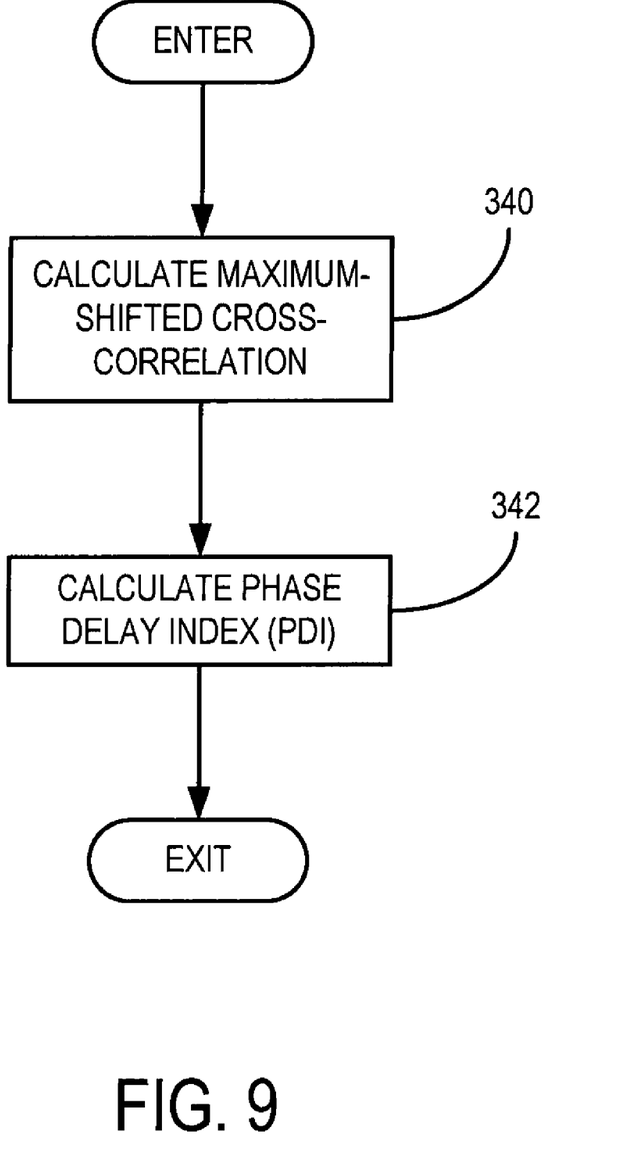
FIG. 9 is a flow chart of steps performed in another one of the steps indicated in FIG. 5

Referring particularly to FIG. 9, the calculation of the PDI connectivity index begins by calculating the maximum-shifted cross-correlation matrix $CC_{ij}^m$ as indicated at process block 340. This is calculated according to the above equation (15) using the voxel vectors 335 and 338 shown in FIG. 7. The cross-correlation of the voxel vectors 335 and 338 is calculated in an iterative process in which the phase of the two vectors are shifted relative to each other until the maximum correlation value is found. The array $CC_{ij}^m$ is the resulting matrix of maximum correlation values.

As indicated at process block 342, the phase delay index is calculated next using the values in the respective matrices $CC_{ij}$ and $CC_{ij}^m$ and the above equation (21). This calculation employs the corresponding values in the arrays $CC_{ij}$ and $CC_{ij}^m$ and it provides the phase delay index (PDI) despite the fact that there may be multiple phase shift amounts that will produce the maximum cross-correlation value at any voxel due to the periodic nature of the acquired NMR signal.

The measurement of the PDI connectivity index provides an opportunity to objectively study mild cognitive impairment (MCI) subjects. By measuring the connectivity index and its rate of change in MCI patients, we may be able to determine who is destined to develop Alzheimer's disease, who is in the critical phase to develop Alzheimer's disease, and who is undergoing normal aging processes. Also, this method may be very useful to monitor responses and evaluate the efficacy of pharmacological intervention involving symptomatic or preventive drugs. Furthermore, the PDI connectivity index may provide an early marker for Alzheimer's disease in individuals who have no clinical symptoms of Alzheimer's.

The functional connectivity measured according to the present invention may also be used to detect or measure the progress of other brain disorders. For example, some disorders may be detected by measuring the connectivity between regions in one hemisphere of the brain and regions in the other hemisphere of the brain. In other brain disorders the connectivity level indicating presence of the disease may require separate measurement of other regions of the brain. For example, the connectivity of a region that is not affected by the disease such as the visual cortex part of the brain, may be measured to establish a preset connectivity level which indicates the boundary between normal and diseased connectivity in the region of the brain being examined for disease. In other words, the connectivity level indicating presence of a disease need not necessarily be a fixed connectivity index, but may instead be a connectivity level relative to a non-diseased region of the brain or to a specific region of the brain.

In the preferred embodiment described above a single 10.5 minute dynamic time course study was acquired. In this preferred embodiment the period 1 data is acquired while the subject is performing Task B. However, the scan may also be repeated with the subject performing Task A during period 1 or the subject may be directed to simply look at a blank screen and do nothing. The present invention may thus measure brain synchrony when performing declarative memory-encoding tasks or when performing nondeclarative memory-encoding tasks. The functional synchrony measured with the present invention may be utilized as a biomarker for localized pathophysiological functions in the brain in contrast to the functional synchrony measured during the resting condition.

We claim:

1. A method for producing an index indicative of the presence of a disease in the brain of a subject, the steps comprising:
   a) acquiring with a magnetic resonance imaging (MRI) system a period of time course image data from the brain of the subject;
   b) acquiring with the MRI system a second period of time course image data from the brain of the subject while the subject performs a task according to a prescribed pattern;
   c) processing the time course image data acquired in step b) to produce an indication of locations in the brain that are neuronally active when the task is performed;
   d) selecting locations in the brain to be included in the calculation of a index using the location indications produced in step c); and e) calculating the index using the time course image data acquired in step a) from the locations selected in step d); wherein step c) includes:

reconstructing a first series of images from the time course image data acguired in step a);

reconstructing a second series of images from the second time course image data acguired in step b); and identifying voxels in the second series of images that are indicative of locations in the brain.

2. The method as recited in claim 1 in which the index is a connectivity index and step e) includes calculating low frequency component voxel vectors from the series of images.

3. The method as recited in claim 2 in which the subject is directed to perform a resting task during the acquisition of time course image data in step a).

4. The method as recited in claim 1 in which step d) includes manually selecting a region in the subject's brain to be included in the index calculation prior to selecting the locations to be included in the index calculation.

5. The method as recited in claim 4 in which the index indicates the presence of Alzheimer's disease and the manually selected region includes the hippocampus.

6. The method as recited in claim 4 in which the index indicates mild cognitive impairment and the manually selected region includes the hippocampus.

7. The method as recited in claim 1 in which the calculation of the index in step e) includes:

e)i) forming a voxel vector, from the second series of images reconstructed in step C), for each location selected in step d);

e)ii) calculating a low frequency component voxel vector from the first series of reconstructed images for each selected location; and e)iii) calculating the cross-correlation between each low frequency component voxel vector and voxel vectors at other ones of the selected locations.

8. The method as recited in claim 7 in which the calculation of the index in step e) also includes:

e)iv) calculating a maximum cross-correlation between each low frequency component voxel vector and said voxel vectors at other ones of the selected locations; and e)v) calculating the index using both the cross-correlation values and the maximum cross-correlation values.

9. The method as recited in claim 8 in which the calculation of the index includes calculating the ratio of the corresponding cross-correlation and the maximum cross-correlation values.

* * * * *

UNITED STATES PATENT AND TRADEMARK OFFICE
CERTIFICATE OF CORRECTION

PATENT NO. : 7,577,472 B2
APPLICATION NO. : 11/375347
DATED : August 18, 2009
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this

Seventh Day of September, 2010

David J. Kappos
*Director of the United States Patent and Trademark Office*